United States Patent [19]

House et al.

[11] 4,126,671

[45] Nov. 21, 1978

[54] METHOD FOR DETECTING BOVINE LEUKEMIA VIRAL INFECTION

[75] Inventors: James A. House; Carol House, both of Pipersville, Pa.

[73] Assignee: Pitman-Moore, Inc., Washington Crossing, N.J.

[21] Appl. No.: 715,343

[22] Filed: Aug. 17, 1976

[51] Int. Cl.$^2$ .................. C12K 1/00; G01N 31/00; G01N 33/16

[52] U.S. Cl. .................. 424/12; 23/230 R; 23/230 B; 195/1.1; 195/1.7; 195/1.8; 260/112 B; 260/112 R; 424/86; 424/89

[58] Field of Search .................. 424/8, 12, 86, 89; 195/1.1, 1.7, 1.8; 260/112 R, 112 B; 23/230 R, 230 B

[56] References Cited

PUBLICATIONS

Onuma, J. of The Nat. Cancer Inst., vol. 55, No. 5, Nov. 1975, pp. 1155–1158.

Miller, J. of The Nat. Cancer Inst., vol. 49, 1972, pp. 1459–1462.

Malmquist, Cancer Res., vol. 29, Jan. 1969, pp. 188–194, 196.

Miller et al., Workshop Conference on Bovine Leukosis, Final Programme, Abstracts, Friday/Sat., Oct. 17/18, 1975, 3 pp.

*Primary Examiner*—Anna P. Fagelson
*Attorney, Agent, or Firm*—Salvatore R. Conte

[57] ABSTRACT

A new immunodiffusion test method for determining the presence of bovine leukemia viral infection in cattle.

The method relies upon the formation of a precipitin line resulting from the reaction of glycoprotein antigen with an antibody. The reaction is conducted in a liquid gel medium. By comparing the precipitin line of this test against a standard the presence of bovine leukemia infection can be diagnosed.

Also covered is the immunological composition comprising said antigen and said liquid gel media.

29 Claims, No Drawings

METHOD FOR DETECTING BOVINE LEUKEMIA VIRAL INFECTION

This invention relates to a new immunodiffusion test means for determining the presence of antibodies to bovine leukemia virus glycoprotein antigen in a serum sample. This invention also relates to a new immunological composition comprising a bovine leukemia glycoprotein antigen and a gel-forming material. This composition is in the form of a homogeneous thin layer adapted to receive test serum specimens suspected of bovine leukemia virus infection.

The diagnosis of bovine leukemia is not new but, until the present discovery, there has not been available a reliable, easily performed serological detection means capable of diagnosing weak antibody response. The present invention uses a glycoprotein antigen in the immunodiffusion technique and a comparison against a known sample to provide a more satisfactory means for detecting said antibodies and diagnosing the bovine leukemia infection.

BACKGROUND OF THE INVENTION

Bovine leukemia is a disease which has serious implications for the cattle industry. Studies on the effect of bovine leukemia have been conducted in the United States and Europe and they support the view that this virus is the infectious etiologic agent responsible for the bovine enzootic leukosis associated with lymphosarcoma.

It is difficult to evaluate the actual incidence of this disease in cattle in the United States. Apparently, there are not as many herds in this country that show as high a percentage of tumors as are found in European cattle, but in 1974, more than 4,500 cattle carcasses were condemned in the United States because of lymphosarcoma.

The bovine leukemia virus belongs to the category of viral agents which are known as oncornaviruses, a name for oncogenic and tumorogenic RNA viruses. This oncornavirus generally does not produce a high percentage of tumors in cattle but it is insidious because it may cause abnormalities other than tumors. Among these are infertility and decreased meat and milk production.

The impact of bovine leukemia on dairy and meat production is difficult to assess in the absence of a reliable serological test for the study of the epidemiology of bovine leukemia.

Another difficulty in studying the oncogenic potential of this virus in cattle is the expense of maintaining them over a long enough period of time so as to allow them to develop tumors. In general, using present techniques, it is necessary to study the animals over a period of 5 to 7 years. This could explain why the incidence of disease in the United States is less than in Europe because, on the average, cattle in this country are slaughtered within about their fourth or fifth year, whereas, many animals in European herds are kept for 10 to 12 years or longer.

Studies have also shown that there appears to be more animals infected in dairy herds than in beef herds. This could very well be due to the management of the various herds. Dairy herds have more contact with pooled colostrum and nurse cows, and more intimate contact with infected animals then do beef animals who generally nurse their own calves and are kept a greater distance from other beef cows.

The bovine leukemia disease appears to be one that is not highly contagious, but it can spread horizontally, that is, from one animal to another in a herd. Bovine leukemia virus can result in a persistent lymphocytosis in some cattle and this condition has been related epidemiologically to a pre-cancerous state. In some countries lymphocytosis is used as a means of detecting and attempting to eradicate bovine leukemia but studies have shown that many cattle develop tumors without developing that condition. However, animals which do not exhibit lymphocytosis are still susceptible to infection and to the oncogenic potential of the virus and, therefore, they can still develop tumors. For this reason, it is generally believed that bovine leukemia canot be eradicated solely on the basis of lymphocyte counts.

It is known that cattle infected with bovine leukemia virus develop persistent infections and most, if not all, of these infected animals develop specific and detectable antibodies. Numerous serological studies have been conducted and they show that the presence of these antibodies are the result of infection with the bovine leukemia virus which produces viral antigens and a correlative antibody response.

Immunodiffusion reaction techniques have been used for the detection of antibodies to an ether resistant antigen of bovine leukemia virus [J. M. Miller, et al.; Journal of the National Cancer Institute, Vol. 49: pages 1459–1462 (1972)].

This technique consists of an immunoprecipitin reaction between an antigen and an antibody in a semi-solid gel medium such as agar. The antigen and antibody are initially soluble in the said medium to the extent that they diffuse or permeate through the matrix material but the reaction product resulting from their combination is insoluble and may be observed visually. The strength of the antigen must be such that it will form a precipitin line of identity with the antiserum in the semi-solid gel medium.

Unfortunately, the bovine leukemia antigen previously used in immunodiffusion tests elicits a very weak antibody response. That antigen, designated by Onuma, et al.,* as an ether-stable molecule (gs-Ag), is an internal antigen of the bovine leukemia virus. Numerous studies with gs-Ag indicate the presence of antibodies but, since the antibody response is very weak, that antigen cannot serve as the basis for a reliable diagnostic test.

*M. Onuma, et al.; Journal of the National Cancer Institute, Vol. 55: No. 5, pages 1155–1158 (November, 1975).

THE INVENTION

A second antigen of the bovine leukemia virus, sensitive to ether, has been found. This antigen appears to be a glycoprotein and studies show that it is a more satisfactory antigen than gs-Ag for the serologic detection of cattle infected with bovine leukemia virus. Based on column chromatography, it is a larger molecule than gs-Ag. It is sensitive to ether and, unlike the internal and ether-stable gs-Ag, it appears to be an external antigen associated with the outside of the virus. On the basis of these and other characterizations M. Onuma et al. (ibid.) concluded that this antigen appears to be a glycoprotein and, hereinafter, it will be referred to accordingly.

It is an object of this invention to describe a novel preparation comprising the glycoprotein bovine leukemia antigen in admixture with a semi-solid gel medium. The said preparation is in the form of a thin layer having at least one well therein and suitable for use in an immunodiffusion reaction.

Another object of this invention is to describe a diagnostic test for diagnosing bovine leukemia virus infection using the said glycoprotein antigen in immunodiffusion reaction techniques. The basis for this test is the concurrent migration of glycoprotein antigen and its corresponding antibodies toward each other through a semi-solid gel medium to form a precipitin line. By comparing the precipitin line against a standard, the presence or absence of the viral infection can be determined. Reference sera serve as a control for the sensitivity of the test.

It is another object of this invention to determine the prior exposure of an animal to bovine leukemia virus using glycoprotein bovine leukemia antigen in a similar immunodiffusion test system.

Still another object of this invention is to describe an immunodiffusion test kit which contains the essentials needed to make a determination on the presence or prior exposure of an animal to bovine leukemia viral infection.

The above objects are accomplished by preparing an immunodiffusion plate comprised of a semi-solid gel medium capable of accommodating the serum samples which are to be tested, and a standardized sample for comparative purposes. The test serum samples are arranged in a pattern by placing onto the gel: (1) glycoprotein bovine leukemia antigen, (2) the suspect serum containing possible antibodies, and (3) the standardized sample (antiserum) extracted from an animal which has survived bovine leukemia infection.

The glycoprotein antigen and the serum antibodies, if any are present, migrate toward each other through the gel and, upon contact, from a visible precipitate. Hereinafter, this visible precipitate will be referred to as a precipitin line.

By comparing the precipitin line against those preduced by reference sera of known strength the presence of infection can be determined.

In general, this method is conducted by providing a pattern of several wells in a layer of semi-solid gel medium. The dimensions of these wells are not critical but, as a practical matter, it is preferable that the wells be uniformly shaped, equal in size and evenly spaced from one another. In practice, the wells generally measure 7 millimeters in diameter and they are spaced about 3 mm apart around a central well or reservoir of the same diameter containing bovine leukemia antigen. A reagent serum (antiserum) which reacts with the bovine leukemia virus antigen to form a distinct precipitin line, is placed in alternate wells. The remaining wells contain the test sera.

The presence of antibodies in the test serum is determined by visually observing the precipitin line which may form between the antigen well and the test serum well and comparing it against the precipitin line which forms between the antigen well and the reagent well. The position of the precipitin line between their respective wells, their clarity in the agar composition and their shape, can be interpreted by the trained observer as an indication of antibody presence in the test serums.

This method relies on a comparison of the precipitin lines which form between the antigen well and the reagent wells in a single pattern. However, a preferred embodiment of this invention relates to the use of a second pattern on the immunodiffusion plate. According to this embodiment a second pattern, identical to the first, is cut into the said plate some distance apart from the first pattern. This second pattern is known as the "Model" pattern.

The wells of the "Model" pattern are filled with bovine leukemia antigen, reference sera and reagent serum of known strength and capable of producing distinct precipitin lines. By comparing the precipitin lines of this pattern with those produced by the suspect serums of the first pattern, a diagnosis on the presence of bovine leukemia antibodies can be made.

The success of this method depends upon the development of a control precipitin line resulting from the contact of the viral glycoprotein antigen with the antibody specific to it. The strength of the antigen must be relatively high. Also, the antiserum (antibody) strength must be such that it will form a visible precipitate with the antigen. Both the antigen and the antibodies in the antiserum must be soluble in the semi-solid gel medium so that they can diffuse through the gel to form the precipitate or precipitin line.

More specifically, this method for determining the presence of bovine leukemia virus comprises:
(1) taking a blood serum sample from the bovine suspected of bovine leukemia virus infection;
(2) diffusing said sample in a gel medium which contains a soluble glycoprotein antigen prepared from infected mammalian or avian cell cultures;
(3) observing the precipitin line which forms when said antibody comes into contact with the said antigen and, optionally,
(4) comparing the observation (3) against a standard in a semi-solid gel medium using reference sera, reagent serum and antigen of known strength to determine infection.

The glycoprotein antigen (2) used in this method may be obtained from any source provided it is substantially pure, that is, it should be substantially free from contamination with specific antibodies and specific in its reaction with antibodies so that upon contact with an antibody to bovine leukemia virus it forms a precipitate to indicate the presence of said virus in the test animal.

The soluble glycoprotein antigen which is used in this process will be described hereinafter in greater detail but, in general, it can be described as an ether labile material obtained from an extract of tissue culture origin. In general, said tissues may be obtained from the mammalian and avian classes of animals as, for example, from monkeys, bats, pigs, sheep, cows, chickens or horses and the like. Typical of the organs from which the said tissues may be obtained are, for example, the kidneys, spleen, leukocytes or testicles of said animals.

Alternatively, the bovine leukemia antigen can be obtained as an extract from animals which have been infected with the virus. Again, it is essential that the antigen not be substantially contaminated or associated with antibodies so that it will be viable for reaction with any antibodies which may be present in the serum samples.

More specifically, the test method of this invention comprises:
(1) placing in separate wells on an immunodiffusion plate:
    (a) a glycoprotein antigen extracted from a tissue culture obtained from the organ of a mammalian or avian animal infected with bovine leukemia virus, (b) an antiserum, for said virus which provides a specific, distinct precipitin line when in contact with the antigen, (a) and (c) the test serum of the suspect bovine;

(2) observing the response thereto, a positive response being indicated by a precipitin line of identity or bending between the antigen-containing well, the antiserum-containing well and the test serum-containing well; and optionally, (3) comparing the observation (2) against standards within the same immunodiffusion plate, said standards comprising a glycoprotein antigen, an antiserum and sera of known strength.

The glycoprotein antigen (a) of this method may be obtained from any source provided it is substantially pure, that is, it should be substantially free from contamination with specific antibodies and specific in its reaction with antibodies so that upon contact with an antibody against bovine leukemia antigens it forms a precipitate to indicate the presence of said virus in the test animal.

Antibodies may appear in cattle within about six to eight weeks after they have been experimentally infected with bovine leukemia virus. The present method is sensitive to the presence of antibodies and correlates their presence with a qualitative determination of infection.

A positive test results in the formation of a precipitin line between the antigen well and the serum well due to the migration of antibodies from the serum well and the migration of antigen from the antigen well. In other words, a positive test indicates the presence of antibodies and is evidence that the animal has been infected by bovine leukemia virus.

A negative test indicates the absence of antibodies. However, since antibodies appear 6 to 8 weeks after experimental infection, all negative animals exposed to possible sources of infection should be isolated and retested at regular intervals until 8 weeks have elapsed. Only in this manner can it be determined that a truly negative group of animals has been obtained. It is also possible that under natural exposure to bovine leukemia virus a longer time may be required to develop antibodies.

Antigen Preparation

The antigen which is used to practice this invention is obtained from mammalian or avian cell cultures infected with bovine leukemia virus (BLV).

A second method comprises extracting the antigen from infected tissues and concentrating the resulting solution.

Antigen is also prepared from the supernatant of mammalian or avian cell cultures infected with bovine leukemia virus. The tissue culture fluids are concentrated using ultrafiltration, dialysis, lyophilization or any concentration technique which preserves the activity of the glycoprotein antigen.

Preferably, the antigen is obtained by extracting it from cell cultures infected with bovine leukemia virus as, for example, cultures from infected fetal lamb spleen cells. According to this method, cell cultures obtained from fetal lamb spleen are inoculated intravenously with bovine leukemia virus. Fluids and tissue cultures are then harvested from the infected fetal lamb spleen cells and this material is subjected to centrifugation.

The supernatant liquid obtained from the centrifugation step is concentrated by forced dialysis and the resulting concentrated supernatant is removed for use as the antigen in the immunodiffusion study.

In the event that the supernatant antigen is intended for future use, then it is most desirable to freeze the liquid so as to assure antigen viability during the storage period.

The viral antigen obtained from the infected cells may be a combination of the ether-stable antigen gs-Ag and the ether-labile glycoprotein antigen (Gp). The gs-Ag antigen produces a very weak antigenic response in bovine animals, but the Gp antigen maintains relatively high titers of antigencity and, therefore, it is more sensitive and reliable in detecting infected animals. Table I shows the relationship of antibodies detected using gs-Ag antigen compared against the Gp antigen.

TABLE I
COMPARISON OF Gp AND gs-Ag ANTIGENS IMMUNODIFFUSION TEST FOR DETECTING ANTIBODY TO BLV

|  |  | Gp Antigen | |
| --- | --- | --- | --- |
|  |  | + | − |
| gs-Ag Antigen | + | 22 | 0 |
|  | − | 25 | 17 |

Both tests agree that there are 22 animals positive and 17 animals negative. However, in 25 cases the test using glycoprotein antigen (Gp antigen) is positive while the gs-Ag antigen test is negative. These represent 25 animals that are infected but undetected by the gs-Ag antigen.

Table II demonstrates in more detail the relationship of these two tests in immunodiffusion test studies:

TABLE II
ANIMALS WITH ANTIBODY TO BLV: Gp AND gs-Ag ANTIGEN

| POSITIVE gs-Ag, POSITIVE Gp: | 22/64 | 34% |
| --- | --- | --- |
| NEGATIVE gs-Ag, POSITIVE Gp: | 25/64 | 39% |
| POSITIVE gs-Ag, NEGATIVE Gp: | 0/64 | 0% |
| NEGATIVE BOTH: | 17/64 | 27% |
| TOTAL | | 100% |

Both tests show 22/64 animals positive, that is 34%. However, the gs-Ag test is negative and the Gp antigen test is positive for 25/64, that is 39% are missed by the gs-Ag test. There are no animals positive on the gs-Ag test that are negative on the Gp immunodiffusion test and both tests agree that 27% are negative. Based on these studies the immunodiffusion ether labile test of this invention using Gp antigen is significantly more sensitive (P<0.0005) in detecting antibody against BLV than is the immunodiffusion test employing gs-Ag antigen. Thus, the glycoprotein is a more desirable antigen for the serologic detection of cattle infected with bovine leukemia virus than is the gs-Ag antigen.

The Gp antigen is collected from the culture fluid by conventional concentration techniques as, for example, by dialysis against polyvinylpyrrolidone. This procedure also concentrates the gs-Ag antigen but the Gp antigen can be isolated therefrom by bringing it into contact with a selective chromatographic absorbent. One such absorbent having an affinity for Gp antigen is Con A-Sephrose (manufactured by Pharmacia Fine Chemicals, Uppsala, Sweden).

The antigen composition is poured over the chromatographic absorbent at about room temperature and it is allowed to stand for several hours. Thereafter, the column is washed throughly and the Gp antigen is eluted with 0.1 Molar alpha methyl-D-mannoside. The elution step can be monitored by testing the fractions at a chosen UV absorbance as, for example, at 280 nm; whereafter, the fractions are pooled. The said fractions contain substantially pure Gp antigen.

Antiserum Preparation

The reference antisera are obtained from animals which have survived bovine leukemia virus infection. The infection may be the result of a naturally occurring virus or the virus may be administered experimentally to produce a reference antiserum.

If the concentration of the reagent antiserum is either too low or too great, it will adversely affect the distinctness of the precipitin line which should form between the reagent serum and antigen wells. The reagent serum should afford only one dense, distinct precipitin line when tested with the BLV antigen and this line should form approximately midway between the serum and the antigen wells with no tendency to broaden or fade with time. If the precipitin line is not midway between the antigen well and the reagent serum well, the antiserum can be diluted or concentrated to the desired strength so that the precipitin line is equidistant between the antigen well and the reagent serum well.

Serum with excess antibodies in relation to the antigen concentration, tend to form a broad band instead of the distinct line which is necessary for accurately determining line identity. In such an instance the antiserum can be diluted to the desired concentration so that the precipitin line is a dense, narrow line. Discrete precipitin lines can be obtained with high titer serums but they must be diluted. Serums that give a non-specific cloudy ring around the well should be avoided.

It is essential that the antiserum preparation be selected from animals surviving BLV infection and it should afford only one dense precipitin line when tested with the glycoprotein antigen.

Immunodiffusion Test Plate

The immunodiffusion reaction of this invention may be carried out on any suitable support as, for example, on glass slides or in plastic dishes or the like. The support is utilized by distributing evenly, over its surface, a layer of semi-solid gel medium.

In general, the support medium may be any gelatinous medium in which the antigen and antibodies are reasonably soluble. In addition, this support medium should be essentially free of contaminating substances and, also, it should be either transparent or translucent so that any precipitin line which forms in the semi-solid gelatinous layer can be observed.

In practice, agar has proved a particularly suitable medium for this purpose and, therefore, hereinafter, agar will be referred to as the semi-solid gel medium of choice, with the understanding that other, functionally equivalent media, may be substituted therefor without departing from the spirit of this invention.

The agar solution is prepared by adding Noble's agar to a solution of a borate buffer comprised of sodium hydroxide and boric acid. The agar solution may be buffered to within a pH range of from about 3–10.5, preferably 5–10 and, most preferably 6–9.

A preferred embodiment of this invention consists of adding a salt, such as sodium chloride, to the agar solution comprising the borate buffer. The concentration of salt in this solution may vary within wide limits as, for example, in the range of from about 3.0–120 g. per liter of distilled water but, a range of from about 8.5–100 g. is preferred and a range of from about 60–90 g. of salt per liter of distilled water is most desirable.

One typical solution which we have found to be particularly suitable in the practice of this invention comprises a layer of 0.7% agar on a suitable support or plate. The agar solution is prepared by adding 7 grams of Noble's agar to 1 liter of highly salted borate buffer comprised of sodium hydroxide (2.0 grams) boric acid (9.0 grams) and sodium chloride (70.0 grams) per liter of distilled water. Following the addition of the salted buffer, the agar mixture is boiled until the agar is dissolved.

After the heating step has been concluded, the 0.7% solution of Noble's agar (15 ml.) is poured onto each plate at a temperature of from about 55°–60° C. Petri dishes having an outside diameter of 100 mm can accommodate four seven-well patterns per plate.

The agar is then allowed to harden at room temperature with the lids ajar to allow moist air to escape. It is essential that the plates dry thoroughly because if excess water remains in the plate it can cause dilution of the reagents.

Agar plates can be prepared well in advance of the actual immunodiffusion reaction but best results are obtained with fresh plates because the agar tends to become cloudy with age and thus obscure somewhat the precipitin lines which must be visualized to make a positive interpretation of the test results. The wells are cut into the plate only after it has dried completely.

The precise pattern of the wells on said agar plates is not critical to this invention and, as a practical matter, any pattern which makes a reliable comparison possible may be used. However, according to a preferred embodiment, it is desirable to space the serum wells around the antigen wells in a circular arrangement and equidistant from one another. A template is used to cut a pattern of seven wells, 3mm apart and 7mm in diameter in the agar to the bottom of the plate. The wells are spaced equidistant from one another around a central well or reservoir of the same diameter. A cannula connected to a vacuum line may be used to remove the plugs which are cut into the agar and any residual moisture therein. Using this procedure, four patterns, each with seven wells, are cut into each plate.

As hereinafter described, each agar plate contains four patterns with seven wells in each pattern. One pattern in each plate may be designated as the 'Model' and it receives antigen, the reagent serum, and reference sera of known strength. When this occurs, the 'Model' pattern thus filled is said to be 'standardized'.

The remaining patterns on the same plate are filled with antigen, reagent serum, and suspect sera for animals whose infection to bovine leukemia virus is to be determined. These patterns are designated as 'Test'.

By comparing the precipitin lines which occur between wells in the 'Test' and 'Model' patterns a qualitative determination can be made relative to the presence of antibodies in the animal whose status is in question.

In filling the 'Test' pattern wells, the test serums are placed in alternate wells (approximately 0.08 ml. per well) around the central well using individual pipettes for each transfer. Reagent antiserum (approximately 0.08 ml. per well) is then placed in the three remaining wells. The placing of test serum and antiserum into the wells is made with care to prevent contamination by bacteria and cross contamination with other samples or reagents.

The bovine leukemia antigen (approximately 0.08 ml.) is placed in the center of the 'Test' pattern using a sterile pipette. Again, care is exercised to prevent contamination of the antigen by bacteria and cross-contamination with other samples or reagents.

In addition to avoiding contamination, care should also be exercised to avoid the formation of air pockets in the bottom of the wells or over-filling. Preferably, the wells are filled level with the agar surface and do not have a meniscus.

In filling the wells of the 'Model' pattern, the reference sera, reagent sera and antigen referred to above are used. This standardized material may be part of a kit containing given quantities of antigen, reagent serum and reference sera, labeled 'positive', 'weak positive' and 'negative'. 'Positive' means that the reference serum contains high levels of antibodies. The 'weak positive' indicates sufficient antibodies to afford a positive test. The negative reference serum has essentially no antibodies and indicates no antibody response in the animal at the time of sampling. To avoid contamination and assure the integrity of this study, the 'Model' wells are filled with the same precautions as described for the 'Test' wells.

When both the 'Model' and 'Test' wells have been filled the agar plate is incubated over an extended period, preferably, about 48 hours, in a closed chamber at ambient temperature. In some instances, to achieve optimum results, it may be desirable or necessary to add moisture to the incubator.

Following the incubation, the plate is ready for a determination on the presence of antibodies to bovine leukemia virus. A strong narrow beam of light should be used for this study and, if possible, the lamp should be adjustable to various positions and intensities. Preferably, the observations are made on a dark or black background.

The presence of antibodies in a suspect sample may be determined by comparing it against the 'Model' pattern.

Every 'Model' contains a positive, weak positive and negative reference sera so as to assure a proper sensitivity for the test. These reference sera produce distinctive precipitin reactions which serve as the basis for a comparison against the precipitin lines of the 'Test' pattern.

The following Diagram 1 is an illustration of a typical 'Model'. The "A" and "RS" in this illustration represent antigen and reagent serum, respectively, and, herinafter, they will be referred to accordingly:

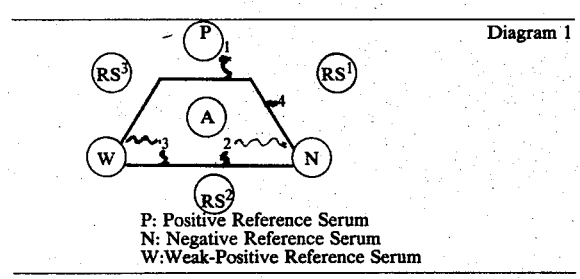

Diagram 1

P: Positive Reference Serum
N: Negative Reference Serum
W: Weak-Positive Reference Serum In this Diagram the precipitin lines or control lines, 1, 2 and 3 are the basis for reading the test.

Precipitin Line 1

The antigen (A) and the antibodies in the positive reference serum (P), migrate toward each other and meet between their respective wells to form a distinct precipitin line 1. Precipitin line 4 turns toward the antigen well (A) before it reaches the well containing the reference serum (P) and it continues on as a line of identity (1) between the reagent serum ($RS^1$) and the antigen. This 'positive' precipitin line 1 indicates infection in the test animal.

Precipitin Line 2

When a serum well has no antibodies it cannot form a precipitin line between its well and the antigen well. Thus, the precipitin line 2 continues into the well (N) without bending. This indicates that there are no detectable antibodies in the negative reference serum (N).

Precipitin Line 3

Line 3 curves at the weak-positive reference serum well (W) but does not form the line of identity which characterizes line 1. This curvature is an indication of a weak antibody response in the reference serum well (W); it shows that the antibody concentration is sufficient to turn precipitin line 3 away and toward the antigen well (A) but insufficient to form a distinct precipitin line between wells A and W. However, since precipitin line 3 curves as it approaches the serum well (W), the serum is considered to possess antibodies. Correlatively, it is also an indication that the serum is from an animal infected with bovine leukemia virus.

The weak antibody reaction illustrated by line 3 is the most difficult to interpret because it can be due to factors other than antibody concentration. Thus, for example, a false 'weak positive' response can occur if there has been seepage of positive control serum under the agar layer into a negative test serum well or, alternatively, a negative sample may be contaminated by a sample containing antibodies. A weak antibody response of this type should be confirmed by a repetition of the test.

Occasionally, a haze will form around a test serum well and this may obscure the precipitin line. Generally, this haze is due to lipids in the serum and, under such circumstances, it is desirable to repeat the test.

Also, on occasion, a positive serum sample may show a second line. This second line may look like a weak positive response when it reaches the reagent serum well but it is generally due to the presence of a second type of antibody to the bovine leukemia virus.

It is generally believed that cattle infected with bovine leukemia virus are virus carriers for life. Therefore, any adult animal that is positive on the immunodiffusion test should be considered infected. Positive serology is not evidence that tumor formation has or will occur because it is widely recognized that tumor formation is an exception rather than the usual result of infection with oncogenic viruses.

As hereinbefore indicated a positive test results in the formation of a precipitin line of identity with the control line or it influences the control line, and this is an indication of antibodies in the test animal. On the basis of this evidence it can be concluded that the animal has been infected by bovine leukemia virus.

A negative test is an indication of the absence of antibodies and it is evidence that if the animal is indeed infected, sufficient time has not elapsed to allow the development of specific antibodies.

This invention will now be described by reference to specific examples. However, it is to be understood that the examples which follow are illustrative only and they are not presented by way of limitation. Any modification of this method which involves simply a variation in the concentration of the reagents or a change in the reaction times or some other such minor adaption, is considered as being within the scope of this invention.

EXAMPLE 1

Immunodiffusion Test Using Gp Antigen

Step A: Cell Culture Production

A cell culture of fetal lamb spleen cells (12 tissue culture passages) was established by standard tissue culture methods. The culture is chronically infected with bovine leukemia virus (BLV) which was passaged 27 times.

Step B: Antigen Preparation (a) Supernatant I: The tissue cultures and fluids from fetal lamb spleen cells, described in Step A, are harvested and a 240 ml sample of this tissue culture fluid is centrifuged for 1 hour at 25,000 RPM at 4° C using an ultracentrifuge.

As a result of the centrifugation there is obtained supernatant liquid and pellets. A sample (200 ml) of the supernatant is placed into dialysis tubing measuring 27/32 inches in diameter. The filled tubing is then placed in a beaker containing 2500 ml of polyvinylpyrrolidone (30% w/v in saline, pH 7.4). A magnetic stirrer is placed into the beaker and the system is agitated at 4° C overnight to approach equilibrium.

The concentrated supernatant (9 ml.) is removed from the dialysis tubing and a 7 ml. sample is taken and held frozen at −70° C for evaluation of antigen content. This sample is identified as supernatant I.

(b) Supernatant II: The remainder of the concentrated supernatant solution (2 ml.) obtained in procedure (a) of this Step B is ether treated by agitating the sample with diethyl ether (2 ml.) for one hour at room temperature (25° C). The ether is then removed by agitation under vacuum. This preparation is frozen at −70° C and put aside for later evaluation of antigen content. The sample is identified as Supernatant II.

(c) Pellet Samples: The pellets resulting from the centrifugation in procedure (a) of this Step B are reconstituted with tissue culture media (5 ml.). The sample is then sonicated to disrupt the particles.

The resultant preparation (5 ml.) is frozen in two portions at −70° C overnight. One sample (3 ml.) is labeled "Raw Pellets" and the second sample (2 ml.) is thawed the next day and ether treated in exactly the same manner as described for the preparation of Supernatat II and labeled "Pellet Ether". All preparations are stored at −70° C.

Step C: Sera from Cattle

Serum was obtained from cattle infected with bovine leukemia virus. The serum contains antibodies which react with antigens associated with bovine leukemia virus.

Step D: Immunodiffusion Test

The immunodiffusion test was conducted for antigen content by using agar gel immunodiffusion techniques employing 0.7% Noble agar in highly salted borate buffer (Composition: sodium chloride 8.5% w/v, boric acid 0.9% w/v and sodium hydroxide 0.2% w/v).

An agar plate using the 0.7% Noble agar composition described in the preceding paragraph was prepared. Immunodiffusion patterns were cut into the agar composition using a template to cut wells which are about 3 mm deep and 7 mm in diameter and spaced equidistant from one another 3mm apart.

The four antigen compositions of this Step, that is, the compositions of subsections (a), (b) and (c) are placed into the center well separated about 3 mm from the peripheral wells. The results of these tests are shown in the comparative patterns of Diagrams 2-5.

In Diagrams 2-5 the wells designated A, B, C and D contain sera from cattle infected with bovine leukemia virus. The center well "X", in each Diagram, contains one of the antigen compositions described in Step B; and the $B^1$ and $B^2$ wells are absent any composition and, therefore, constitute blanks.

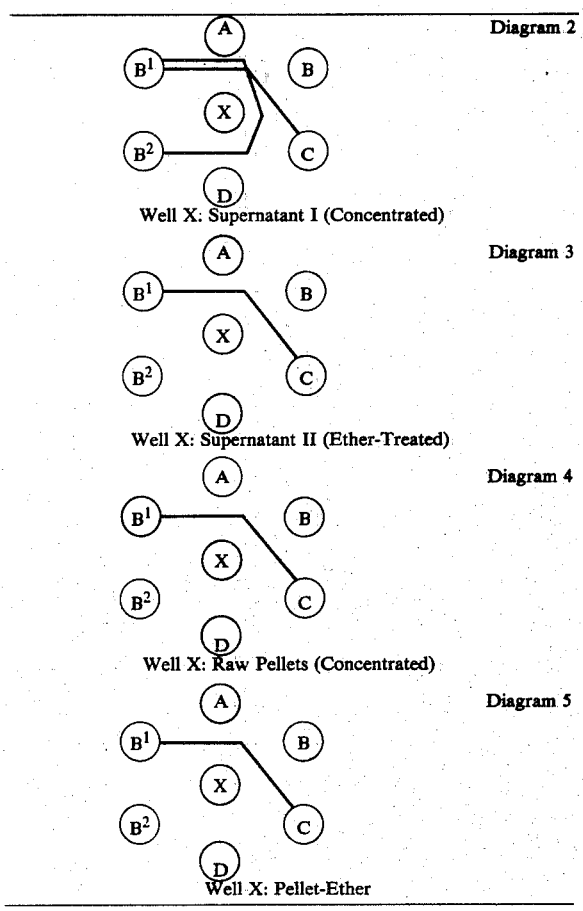

Diagram 2
Well X: Supernatant I (Concentrated)

Diagram 3
Well X: Supernatant II (Ether-Treated)

Diagram 4
Well X: Raw Pellets (Concentrated)

Diagram 5
Well X: Pellet-Ether

Diagram 2: This pattern indicates that sera possess the ability to form two precipitin lines with supernatant which has not been treated with ether.

Diagram 3: This select group of sera forms only one line when reacted with ether-treated supernatant II. Sera initially forming only one line with untreated antigen have no capacity to form a precipitin line with ether-treated antigen.

Diagrams 4 and 5: The pellet samples possess no capacity to form two immunoprecipitin lines with any serum.

On the basis of this study it can be concluded that the antigen of Diagram 2, corresponding to the Supernatant I composition of Step B (a), is most effective in detecting the presence of antibodies in animals infected with bovine leukemia virus. The supernatant I composition (which is not treated with ether), is superior to the ether-treated supernatant II composition of Step B (b) because it detects antibodies in sera which escape detection when the latter is used as the antigen.

This invention has been described by reference to specific embodiments but it is to be understood that various modifications can be made without departing from the spirit of this invention. To the extent that those modifications would be obvious to one skilled in the art they are inherently included as being within the scope of this invention.

What is claimed is:

1. An immunological composition for detecting bovine leukemia virus infection in a bovine animal comprising:
    (1) an ether-labile antigen extracted from cell cultures infected with bovine leukemia virus; in homogeneous admixture with
    (2) a semi-solid gel medium;
said composition being in the form of a thin layer and having at least one well therein adapted to receive a test specimen of an animal suspected of infection by said virus.

2. The immunological composition of claim 1 wherein the antigen is extracted from mammalian or avian cell cultures infected with bovine leukemia virus.

3. An immunological composition according to claim 1 comprising:
    (1) an ether-labile antigen extracted from mammalian cell cultures infected with bovine leukemia virus, said antigen being substantially free from contamination with specific antibodies so that upon contact with an antibody against the bovine leukemia virus it forms a precipitate to indicate the presence of said virus in the test animal; in homogeneous admixture with
    (2) a semi-solid gel medium;
said composition being in the form of a thin layer and having at least one well therein adapted to receive a test specimen of an animal suspected of infection by said virus.

4. The immunological composition of claim 3 in which the antigen is extracted from a mammalian organ infected with bovine leukemia virus.

5. An immunological composition according to claim 1 comprising:
    (1) an ether-labile antigen extracted from fetal lamb spleen cell cultures infected with bovine leukemia virus; in homogeneous admixture with
    (2) an agar medium including borate buffer to pH3–10.5 and 3.0–120g per liter of sodium chloride; said composition being in the form of a thin layer having at least one well therein adapted to receive a test specimen of an animal suspected of infection by said virus.

6. A method for determining the presence of antibodies to bovine leukemia virus in a bovine which comprises:
    (1) taking a blood serum sample from said bovine;
    (2) diffusing the said sample in a gel medium which contains a soluble ether-labile antigen extracted from cell cultures infected with bovine leukemia virus so that upon contact with an antibody to bovine leukemia virus it forms a precipitate or exerts an influence on the precipitin line to indicate the presence of said virus in the test animal;
    (3) observing the presence of the precipitin line which forms when said antibody comes into contact with said antigen or, alternatively, the absence of such a precipitin line.

7. A method for determining the presence of antibodies to bovine leukemia virus in a bovine which comprises:
    (1) taking a blood serum sample from said bovine;
    (2) diffusing the said sample in a gel medium which contains a soluble ether-labile antigen extracted from cell cultures infected with bovine leukemia virus; said antigen being substantially free from contamination with specific antibodies so that upon contact with an antibody against bovine leukemia virus it forms a precipitate, or exerts an influence on the precipitin line to indicate the presence of antibodies to said virus in the test animal;
    (3) observing the presence of the precipitin line which forms when said antibody comes into contact with said antigen or, observing the absence of such a precipitin line; or, alternatively, observing the influence exerted on the precipitin line as an indication of the presence of antibodies to said virus in the test animal; and
    (4) comparing the observation (3) against a model in agar gel medium using reference serums.

8. The method according to claim 7 in which the antigen is extracted from a mammalian organ infected with bovine leukemia virus or is obtained from a lymphocyte suspension culture.

9. The method of claim 6 in which the antigen is extracted from mammalian or avian cell cultures infected with bovine leukemia virus.

10. The method of claim 6 in which the antigen is extracted from mammalian cell cultures infected with bovine leukemia virus.

11. The method of claim 6 in which the antigen is extracted from fetal lamb spleen cell cultures infected with bovine leukemia virus.

12. The method according to claim 6 in which the gel medium contains a concentration of sodium chloride in the range of from about 3.0–120 grams per liter.

13. The method of claim 6 in which the gel medium has a pH within the range of from about 3–10.5.

14. A method of diagnosing the presence of bovine leukemia virus infection in a suspect bovine animal which comprises:
    (1) placing in separate wells on an immunodiffusion plate;
        (a) an ether-labile antigen for said virus which is extracted from cell cultures infected with bovine leukemia virus and having sufficient strength to form a distinct, specific precipitin line with the antiserum(b);
        (b) an antiserum for said virus which provides a specific distinct precipitin line with the antigen(a); and
        (c) the test serum of a suspect bovine animal;
    (2) observing the response thereto, a positive response being indicated by a precipitin line of identity or the influence which the test serum exerts on the line formed by the reagent serum and the antigen.

15. A method according to claim 14 in which the antigen for said virus is extracted from a mammalian organ infected with bovine leukemia virus or is obtained from a lymphocyte suspension culture.

16. The method of claim 14 in which the antigen is extracted from mammalian cell cultures or avian cell cultures.

17. The method of claim 14 in which the antigen is extracted from mammalian cell cultures infected with bovine leukemia virus.

18. The method of claim 14 in which the antigen is extracted from fetal lamb spleen cell cultures infected with bovine leukemia virus.

19. The method according to claim 10 in which the gel medium contains a concentration of sodium chloride in the range of from about 3.0–120 grams per liter.

20. The method of claim 10 in which the gel medium has a pH in the range of from about 3–10.5.

21. A method for detecting antibodies to bovine leukemia virus in a bovine which comprises:
(1) placing a test serum into at least one well in an indicator system comprising;
    (a) a gel medium having homogeneously mixed therein an ether-labile antigen extracted from cell cultures infected with bovine leukemia virus; and
(2) determining the presence of a precipitate, a positive test being in the form of a visible precipitate which results from the combination of said antigen in the gel medium(a) and the antibody of the test serum or the influence which the test serum exerts on the line formed by a reagent serum and the antigen.

22. A method according to claim 21 in which the antigen is extracted from mammalian organs infected with bovine leukemia virus or is obtained from a lymphocyte suspension culture.

23. The method of claim 16 in which the antigen is extracted from mammalian cell cultures or avian cell cultures.

24. The method of claim 21 in which the antigen is extracted from mammalian cell cultures infected with bovine leukemia virus.

25. The method of claim 21 in which the antigen is extracted from fetal lamb spleen cell cultures infected with bovine leukemia virus.

26. The method according to claim 16 in which the gel medium contains a concentration of sodium chloride in the range of from about 3.0–120 grams per liter.

27. The method of claim 16 in which the gel medium has a pH in the range of from about 3–10.5.

28. A method for determining the presence of antibodies to bovine leukemia virus in a bovine which comprises:
(1) taking a blood serum sample from said bovine;
(2) diffusing the said sample in a gel medium which contains a soluble ether-labile antigen extracted from cell cultures infected with bovine leukemia virus so that upon contact with an antibody to bovine leukemia virus it forms a precipitate or exerts an influence on the precipitin line to indicate the presence of said virus in the test animal;
(3) observing the presence of the precipitin line which forms when said antibody comes into contact with said antigen or, alternatively, the absence of such a precipitin line; and
(4) comparing the observation (3) against a model in agar gel medium using reference serum.

29. A method of diagnosing the presence of bovine leukemia virus infection in a suspect bovine animal which comprises:
(1) placing in separate wells on an immunodiffusion plate:
    (a) an ether-labile antigen for said virus which is extracted from cell cultures infected with bovine leukemia virus and having sufficient strength to form a distinct, specific precipitin line with the antiserum (b);
    (b) an antiserum for said virus which provides a specific distinct precipitin line with th antigen(a); and
    (c) the test serum of a suspect bovine animal;
(2) observing the response thereto, a positive response being indicated by a precipitin line of identity or the influence which the test serum exerts on the line formed by the reagent serum and the antigen; and
(3) comparing the observation (2) against a model on a similar immunodiffusion plate comprising the antigen, an antiserum and the reference sera of known strength.

* * * * *